(12) United States Patent
Tabuchi (10) Patent No.: US 8,663,095 B2
(45) Date of Patent: Mar. 4, 2014

(54) MARKER AND GUIDE SHEATH SYSTEM FOR ENDOSCOPIC TREATMENT TOOL

(75) Inventor: Yasuhiro Tabuchi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1173 days.

(21) Appl. No.: 12/146,216

(22) Filed: Jun. 25, 2008

(65) Prior Publication Data

US 2009/0005644 A1    Jan. 1, 2009

(30) Foreign Application Priority Data

Jun. 29, 2007    (JP) ............................... P2007-171851

(51) Int. Cl.
*A61B 1/00*     (2006.01)
(52) U.S. Cl.
USPC .......................................................... 600/127
(58) Field of Classification Search
None
See application file for complete search history.

(56) References Cited

U.S. PATENT DOCUMENTS

| | | | | | |
|---|---|---|---|---|---|
| 3,977,708 | A | * | 8/1976 | Jopp ............................... | 285/342 |
| 4,576,162 | A | * | 3/1986 | McCorkle ....................... | 606/159 |
| 6,210,398 | B1 | | 4/2001 | Ouchi | |
| 6,544,231 | B1 | | 4/2003 | Palmer et al. | |
| 2007/0282205 | A1 | * | 12/2007 | Furia ............................. | 600/461 |
| 2009/0099414 | A1 | * | 4/2009 | Goto et al. ..................... | 600/106 |

FOREIGN PATENT DOCUMENTS

| | | |
|---|---|---|
| DE | 199 24 639 A1 | 12/1999 |
| EP | 0 834 278 A1 | 4/1998 |
| JP | 4-54970 A | 2/1992 |
| JP | 11-258522 A | 9/1999 |
| JP | 2002-545 A | 1/2002 |
| JP | 2004-154485 | 6/2004 |
| JP | 2006-198299 A | 8/2006 |
| WO | WO 2007/055032 A1 | 5/2007 |

OTHER PUBLICATIONS

Japanese Office Action dated Feb. 28, 2012 from corresponding Japanese Patent Application No. 2007-171851, together with an English language translation.
Japanese Office Action dated Oct. 4, 2011 from corresponding Japanese Patent Application Publication No. 2007-171851 together with partial English language translation.

* cited by examiner

*Primary Examiner* — Bill Thomson
*Assistant Examiner* — Scott T Luan
(74) *Attorney, Agent, or Firm* — Scully, Scott, Murphy & Presser, P.C.

(57) ABSTRACT

A marker to be attached to an endoscopic treatment tool for precisely directing a tip of the treatment tool to a target site with no additional physical burden to the patient is provided. A marker 1 used in an endoscopic treatment tool to be inserted in a guide sheath, the marker including: a body 2; and a tip section 4A for removably fixing the body 2 to a middle section of the endoscopic treatment tool, wherein the distance between the body 2 and a tip of the endoscopic treatment tool can be determined freely.

6 Claims, 9 Drawing Sheets

MARKER AND GUIDE SHEATH SYSTEM FOR ENDOSCOPIC TREATMENT TOOL

BACKGROUND OF THE INVENTION

1. Field of the Invention

The present invention relates to a marker and a guide sheath system to be attached to an endoscopic treatment tool. This application claims priority on Japanese Patent Application No. 2007-171851 filed on Jun. 29, 2007, the disclosure of which is incorporated herein by reference.

2. Description of the Related Art

An operator performing an endoscopic biopsy of a peripheral lesion in a lung often locates a target site in a bronchiole. The bronchiole diameter is so small that a usual endoscope tip cannot reach the target site. In some cases, the bronchiole may be branched several times from the tip of the endoscope to the target site, and thus it is difficult to repeatedly make the treatment tool reach the target site after taking biopsy tissue samples at that site.

To address this problem, Japanese Unexamined Patent Application, First Publication No. 2004-154485 discloses a method for biopsy in which a guide sheath having a diameter smaller than that of the endoscope is inserted in a channel of the endoscope, projected from an endoscope tip to be held near a target site, and a treatment tool is inserted in the guide sheath for performing biopsy.

A targeted lesion is often very small. Even if a lesion is detected by using a ultrasonic probe or other instruments, it is difficult for an operator to determine how far the treatment tool such as forceps is to be advanced for performing biopsy after the removal of the ultrasonic probe. Merely several millimeters of misalignment may cause the treatment tool to miss the target site. A problem has currently arisen that it is only after the inspection is completed that the operator finds out whether or not proper tissue samples were taken. In addition, usually the tissue samples are taken five or six times at a site, the above-mentioned problem may occur more often. In fact, accuracy in such a biopsy is currently insufficient.

If the tip position of the treatment tool is observed at all times by X-ray radioscopy, the above problems may be avoided. However, the X-ray radioscopy may expose the patient to radiation in a large amount. Thus, it is a seriously invasive procedure for just an inspection.

SUMMARY OF THE INVENTION

In view of the above, an object of the invention is to provide a marker and a guide sheath system to be attached to an endoscopic treatment tool for precisely directing a tip of the treatment tool to a target site with no additional physical burden to the patient.

The invention is a marker used in an endoscopic treatment tool to be inserted in a guide sheath. The marker includes: a body; and a fixing portion for removably fixing the body to a middle section of the endoscopic treatment tool, wherein the distance between the body and a tip of the endoscopic treatment tool can be determined freely.

With the marker used in the endoscopic treatment tool of the invention, an operator can control the endoscopic treatment tool such that a desired length of the marker inserted in the guide sheath is projected from the guide sheath tip by fixing the marker on the fixing portion at a desired position of the middle section of the endoscopic treatment tool.

The body is formed of an elastic material and includes an insertion hole in which the endoscopic treatment tool is inserted; and the fixing portion is defined by an inner wall of the insertion hole and fixes the body to be slidable in an axial direction of the endoscopic treatment tool due to frictional force generated between the endoscopic treatment tool and the inner wall of the insertion hole.

The marker used in the endoscopic treatment tool of the invention further includes an abutting portion which abuts a base end of the guide sheath, wherein the abutting portion may be made to abut the base end of the guide sheath to allow the tip of the endoscopic treatment tool to project from the tip of the guide sheath by a predetermined amount.

The marker used in the endoscopic treatment tool of the invention further includes an engaging portion to be engaged with the base end of the guide sheath, wherein the engaging portion may be made to be engaged with the base end of the guide sheath to allow the tip of the endoscopic treatment tool to project from the tip of the guide sheath by a predetermined amount.

A guide sheath system for an endoscopic treatment tool includes: a marker used in an endoscopic treatment tool according to the invention; and a guide sheath which includes at a base end thereof an engaging member which is engaged with the engaging portion.

According to the guide sheath system of the invention, the tip of the endoscopic treatment tool can be projected precisely with the marker used in the endoscopic treatment tool engaged into the engaging member provided at the base end of the guide sheath.

The engaging portion of the marker of the endoscopic treatment tool may include a circumferential engaging groove formed in a radial direction outside of the insertion hole, and when the engaging member advances in the engaging groove, the guide sheath and the marker used in the endoscopic treatment tool may engage each other. In this case, the marker used in the endoscopic treatment tool can be securely fixed to the guide sheath.

A wall surface of the engaging groove at the side of the insertion hole may be formed such that the engaging groove has a radial direction width which becomes gradually smaller along an axial direction of the insertion hole from an end at which the engaging member enters; an inner surface of the engaging member may be formed such that a wall thickness of the engaging member becomes thicker in an axial direction of the engaging member from an end at which the engaging member enters the engaging groove; a taper angle of the inner surface of the engaging member may be larger than that of the wall surface at the side of the insertion hole of the engaging groove; when the engaging member advances in the engaging groove, the wall surface at the side of the insertion hole of the engaging groove may be pressed against the insertion hole and the body may be fixed to the endoscopic treatment tool.

With this structure, the guide sheath system can be obtained that firmly fixes the endoscopic treatment tool while sliding resistance during adjustment of the fixing position is small.

According to the marker and the guide sheath system used in the endoscopic treatment tool of the invention, the tip of the endoscopic treatment tool can be precisely positioned at the target site with no additional physical burden to the patient.

DESCRIPTION OF THE PREFERRED EMBODIMENTS

Referring now to FIGS. 1 to 13, a marker used in the endoscopic treatment tool (hereinafter, referred to as "marker") according to an embodiment of the invention will be described.

Figure 1:
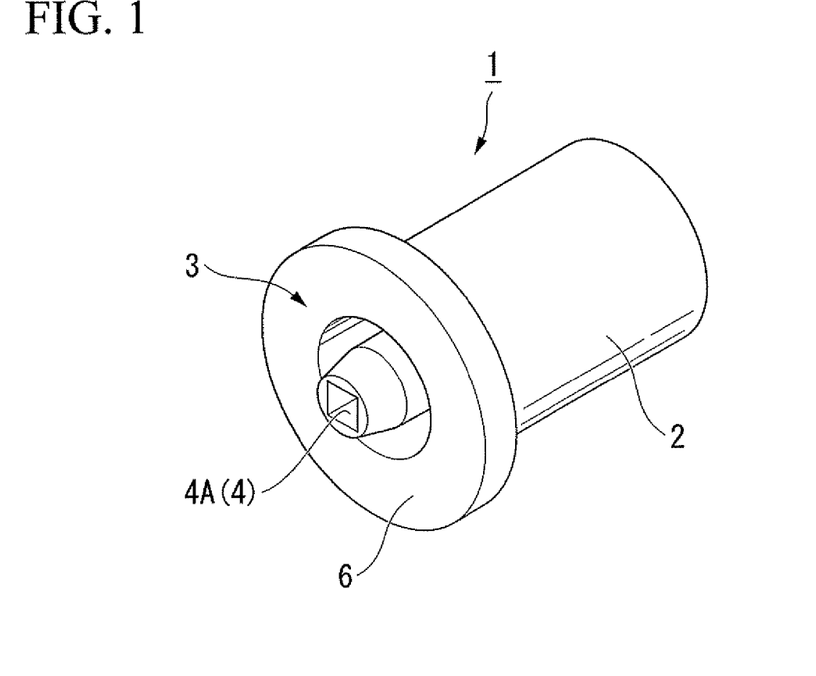
FIG. 1 is a perspective view of a marker used in an endoscopic treatment tool according to an embodiment of the invention.

FIG. 1 is a perspective view of a marker 1. The marker 1 is formed of an elastic material such as silicone rubber. The marker 1 includes a substantially cylindrical body 2 and a engaging portion 3 provided at a front end of the body 2.

Figure 2:
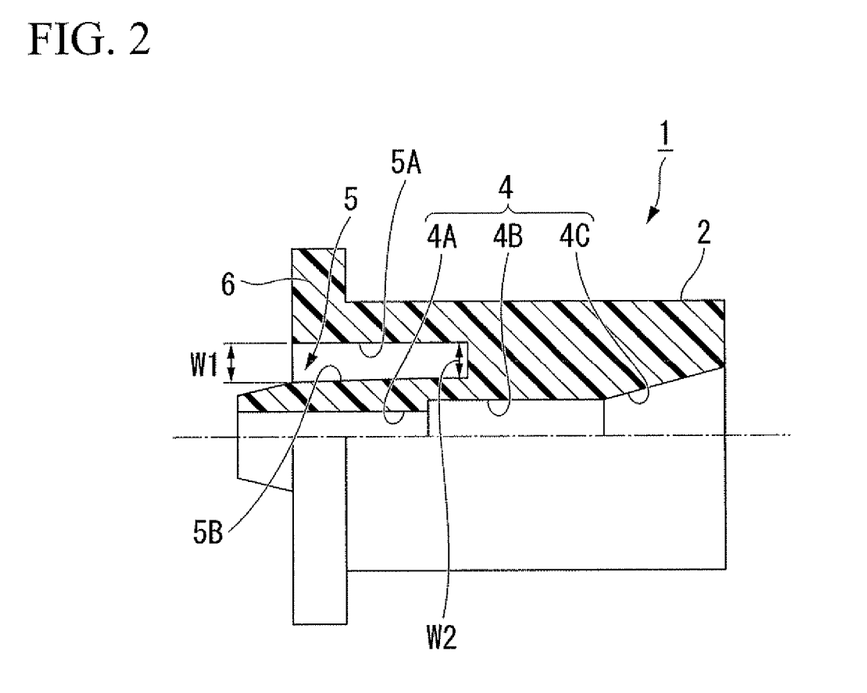
FIG. 2 is a right side view, partially shown in cross-section, of the marker used in the endoscopic treatment tool.

FIG. 2 is a right side view, partially shown in cross-section, of the marker 1. The marker 1 includes an insertion hole 4 along its central axis in which an endoscopic treatment tool is inserted. The insertion hole 4 includes a tip section 4A at the side of engaging portion 3, an inserting section 4C at the side of an opposite rear end, and a middle section 4B between the tip section 4A and the inserting section 4C.

Figure 3:
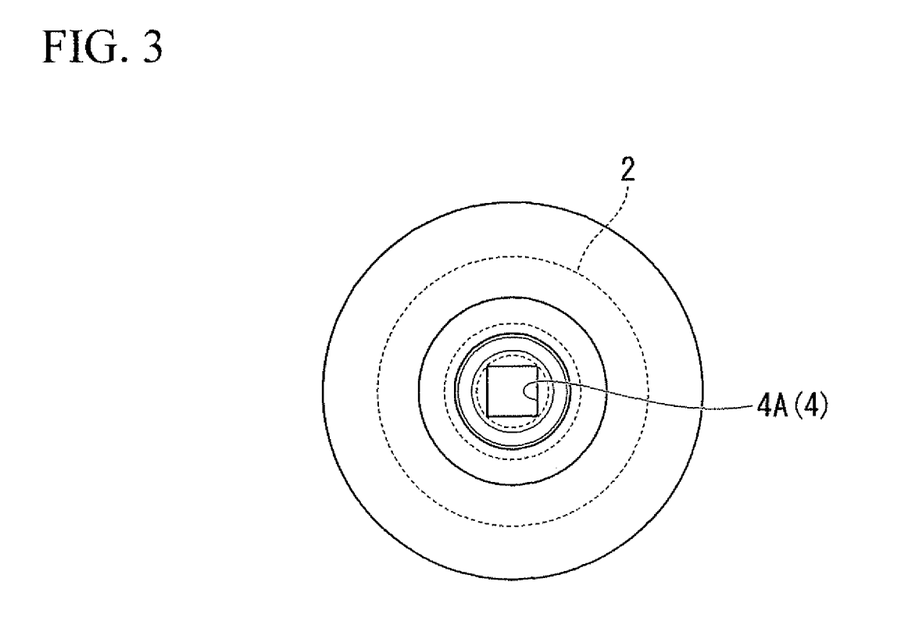
FIG. 3 is a front view of the marker used in the endoscopic treatment tool.

As shown in FIGS. 1 and 3, the tip section 4A is square-sectioned and functions as a fixing portion for fixing the body 2 to an intended position of the middle section of the endoscopic treatment tool due to frictional force generated at the contact face of the tip section 4A and the external surface of the endoscopic treatment tool as described later.

The middle section 4B is circular-sectioned and has a diameter larger than the maximum inner diameter (i.e., the diagonal diameter in the cross-section) of the tip section 4A. Thus, the middle section 4B does not come in direct contact with an external surface of the endoscope treatment tool.

The inserting section 4C is also circular-sectioned and has a diameter that is substantially the same as that of the middle section 4B at the side of the middle section 4B and gradually expands toward the rear end. Namely, the inserting section 4C is formed in a tapered shape such that the endoscopic treatment tool may be easily inserted from the expanded rear end of the insertion hole 4. The marker 1 is removably attached to the endoscopic treatment tool. In particular, after the endoscopic treatment tool is inserted from the inserting section 4C and the marker 1 is attached, the endoscopic treatment tool can be removed.

The engaging portion 3 includes an annular engaging groove 5 provided in a circumferential direction thereof on a radial direction outside of the insertion hole 4, and a flange 6 circumferentially projecting from the radial direction outside of the engaging groove 5.

The engaging groove 5 is provided between the external surface of the tip section 4A of the insertion hole 4 and the body 2 concentrically with the insertion hole 4. A guide sheath is engaged in the engaging groove 5 as described later.

As shown in FIG. 2, the engaging groove 5 includes a first surface 5A at the side of the flange 6 formed substantially parallel with the axial direction of the marker 1, and a second surface (wall surface) 5B at the side of the insertion hole 4 formed such that a radial direction width W1 of the engaging groove 5 at the front end is slightly larger than a radial direction width W2 at the rear end. That is, the engaging groove 5 is tapered such that the radial direction width thereof becomes smaller toward the axial direction of the insertion hole 4.

Figure 4:
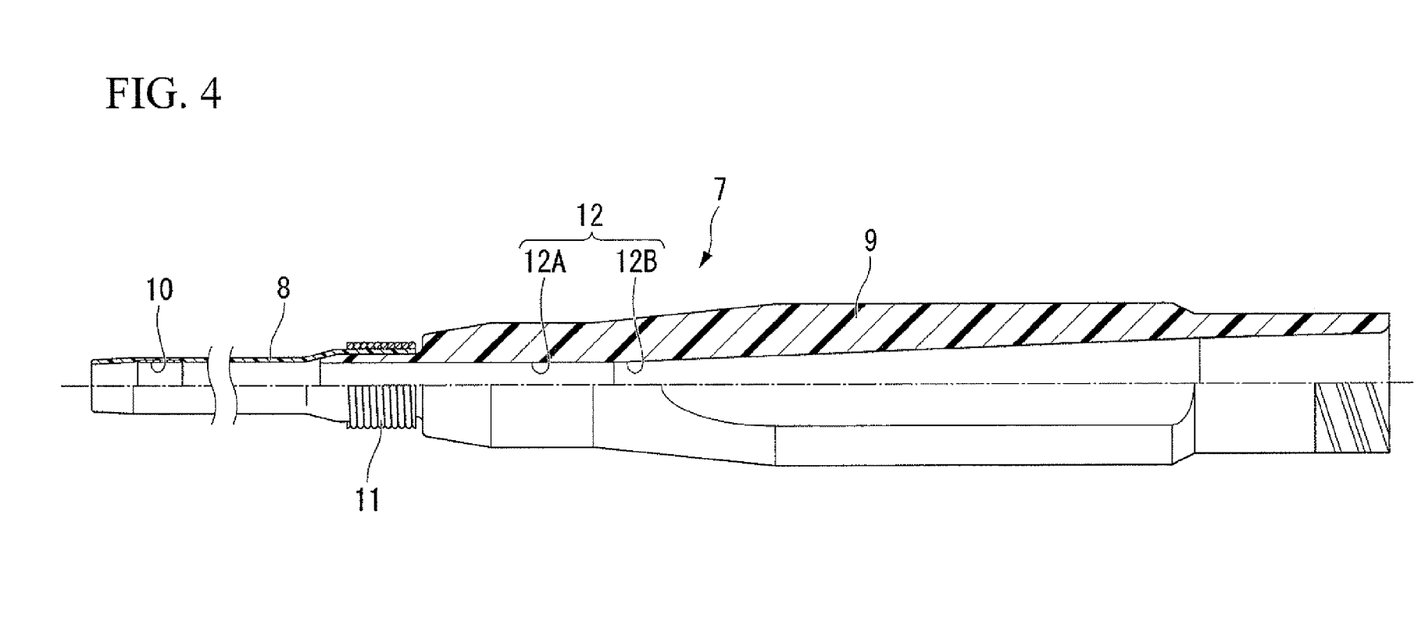
FIG. 4 is a partial cross-sectional view of a guide sheath used with the endoscopic treatment tool.

FIG. 4 is a partial cross-sectional view of a guide sheath 7 used with the marker 1. The guide sheath 7 includes a tubular, flexible sheath body 8 made of, for example, resin, and a stick (engaging member) 9 attached to a base end of the sheath body 8.

As shown in FIG. 4, a tubular indexing member 10 made of stainless steel or the like is thermoformed at an inner surface of the sheath body 8 near the tip thereof. With the X-ray radioscopy, the indexing member 10 is an indication of the tip position of the sheath body 8. A base end of the sheath body 8 is press-fit at the tip of the stick 9 and is fixed by a coil 11 from the outside.

The stick 9 is a tubular member made of resin or the like, and includes a through hole 12 inside thereof. An endoscopic treatment tool is inserted in the through hole 12. The through hole 12 is circular-sectioned and includes a first section 12A with a constant diameter and a second section 12B with a diameter gradually expanding toward the rear end. The inner surface of the second section 12B is formed such that the wall surface of the stick 9 becomes thicker in the axial direction of the stick 9 from the rear end where the stick 9 enters the engaging groove 5 of the marker 1. The taper angle of the inner surface of the second section 12B is larger than that of the second surface 5B of the engaging groove 5 of the marker 1.

Figure 5:
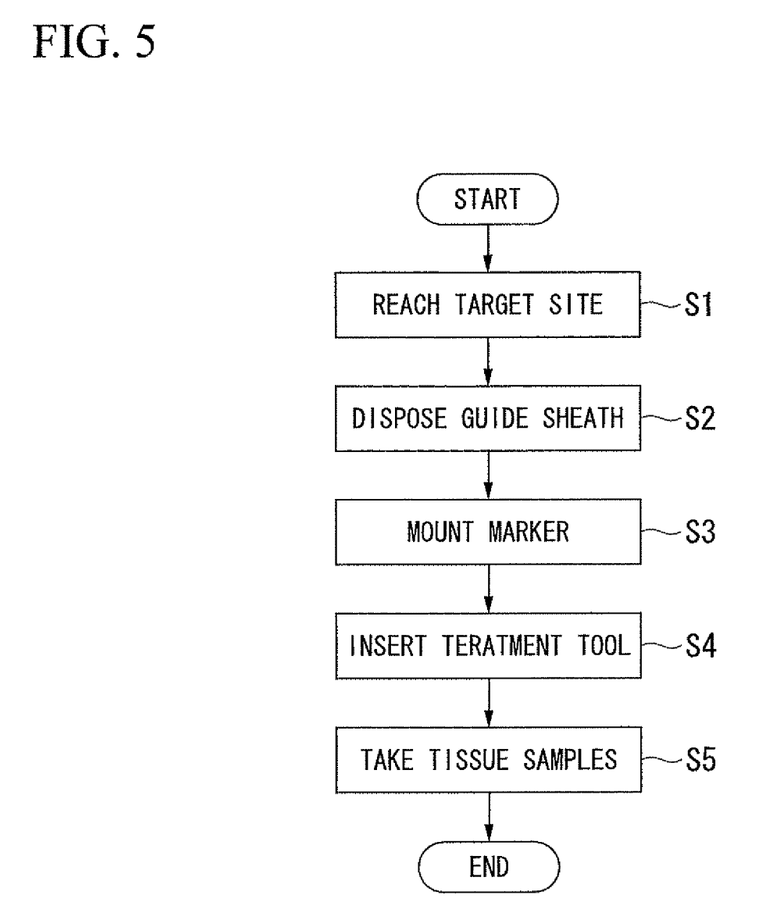
FIG. 5 is a flow chart illustrating the procedure of lung biopsy using the marker used in the endoscopic treatment tool.

Referring now to FIGS. 5 to 13, an operation of the marker 1 and the guide sheath 7 will be described. FIG. 5 is a flow chart illustrating a procedure of lung biopsy using an endoscopic treatment tool performing with the marker 1 and the guide sheath 7.

First, in step S1 shown in FIG. 5, the guide sheath 7 is moved to the target site where tissue samples are to be taken. In particular, the endoscope is advanced within a bronchus while the position of the target site is observed through X-ray radioscopy images.

Figure 6:
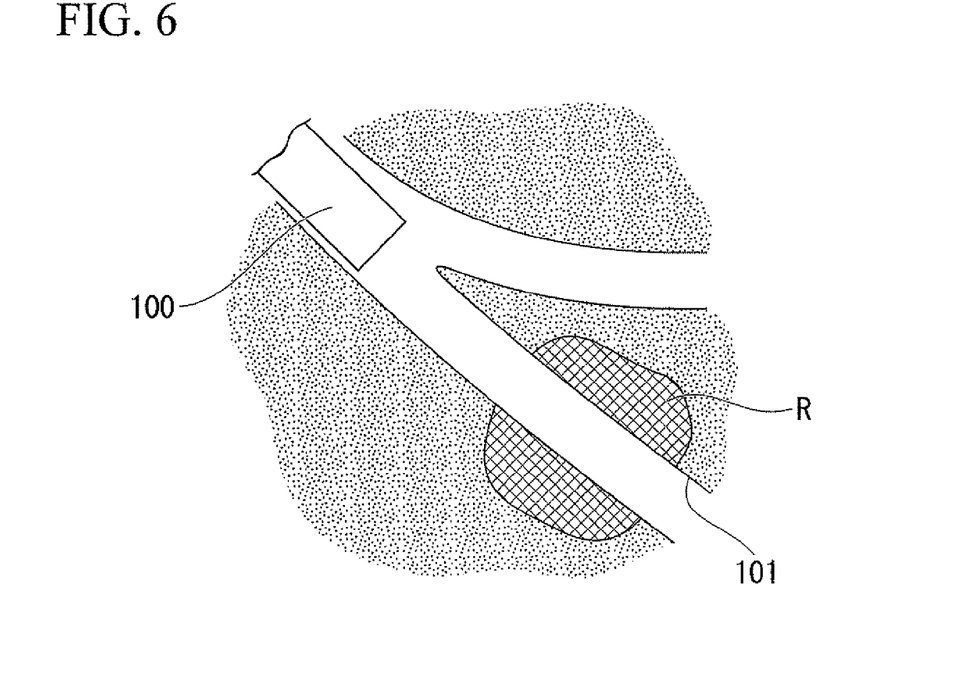
FIG. 6 is a view illustrating a state in which the endoscope is moved near the target site.

FIG. 6 illustrates a state in which an endoscope 100 is advanced to the vicinity of a target site R. Since the diameter of a bronchiole 101 in which the target site R exists is smaller than that of the endoscope 100, the endoscope 100 cannot be advanced further toward the target site R.

Figure 7:
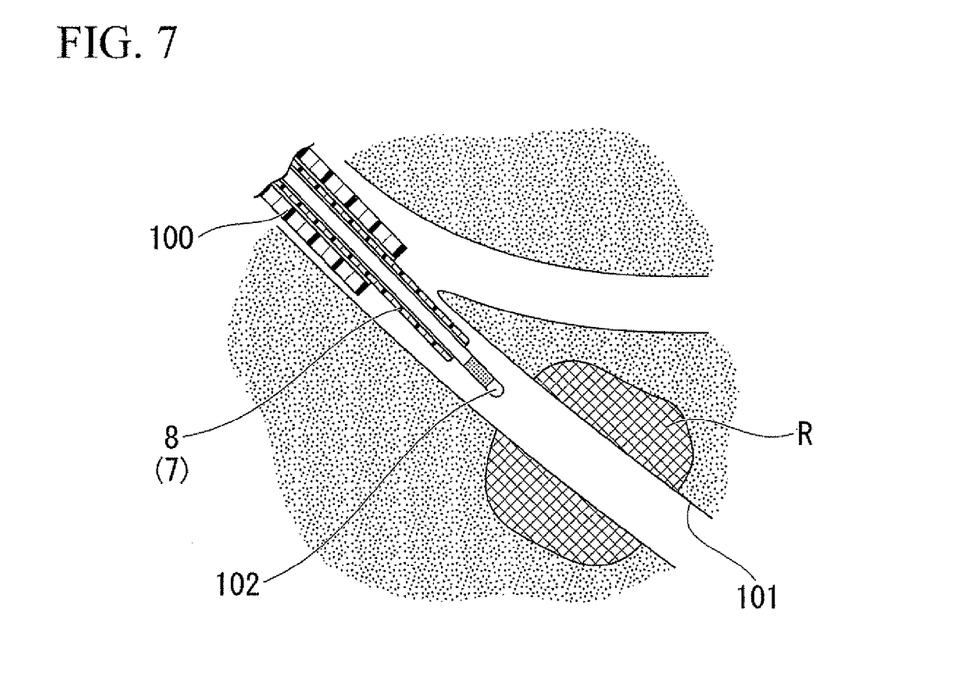
FIG. 7 is a view illustrating a state in which an ultrasonic probe is projected from the endoscope.

Here, an ultrasonic probe 102 placed in the guide sheath 7 is inserted together with the guide sheath 7 from an opening for forceps (not shown) of the endoscope 100 and is projected from the tip of the endoscope 100 as shown in FIG. 7. Since the diameters of the sheath body 8 and the ultrasonic probe 102 of the guide sheath 7 are smaller than that of the endoscope 100, the guide sheath 7 can reach the target site R through the bronchiole 101.

Figure 8:
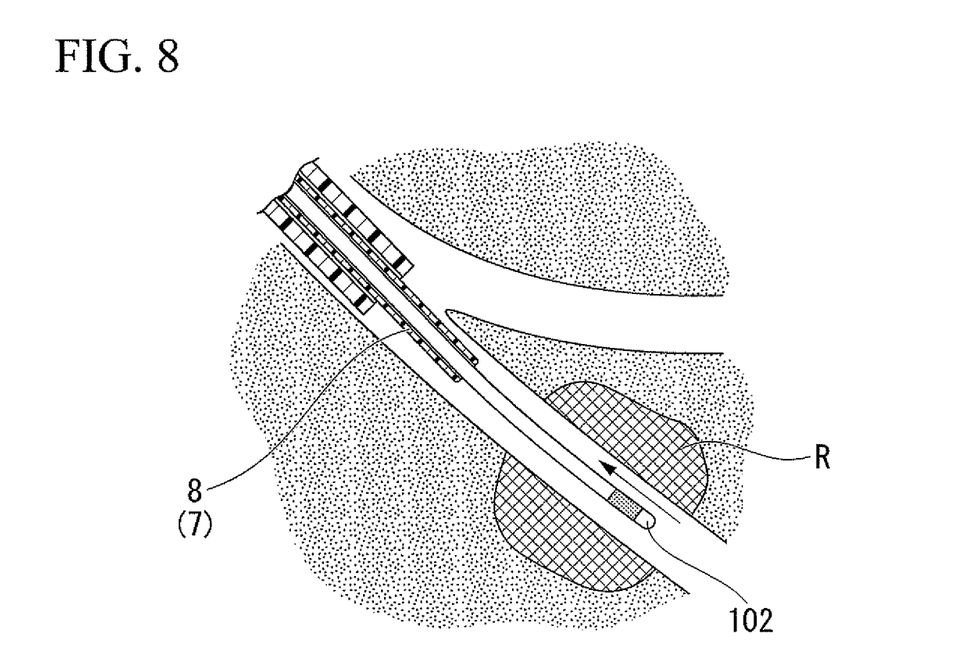
FIG. 8 is a view illustrating a state in which an image of the target site is obtained with the ultrasonic probe.

As shown in FIG. 8, the sheath body 8 itself is stopped at a position considered near but not touching the target site R, and the ultrasonic probe 102 is moved ahead to a position beyond the target site R. Then, the ultrasonic probe 102 is slowly pulled back in the direction of an arrow in FIG. 8.

Images of the tissue around the ultrasonic probe 102 are displayed on unillustrated test equipment through the ultrasonic wave emitted from the ultrasonic probe 102. Thus, the operator can confirm whether the ultrasonic probe 102 has reached the target site R.

Figure 9:
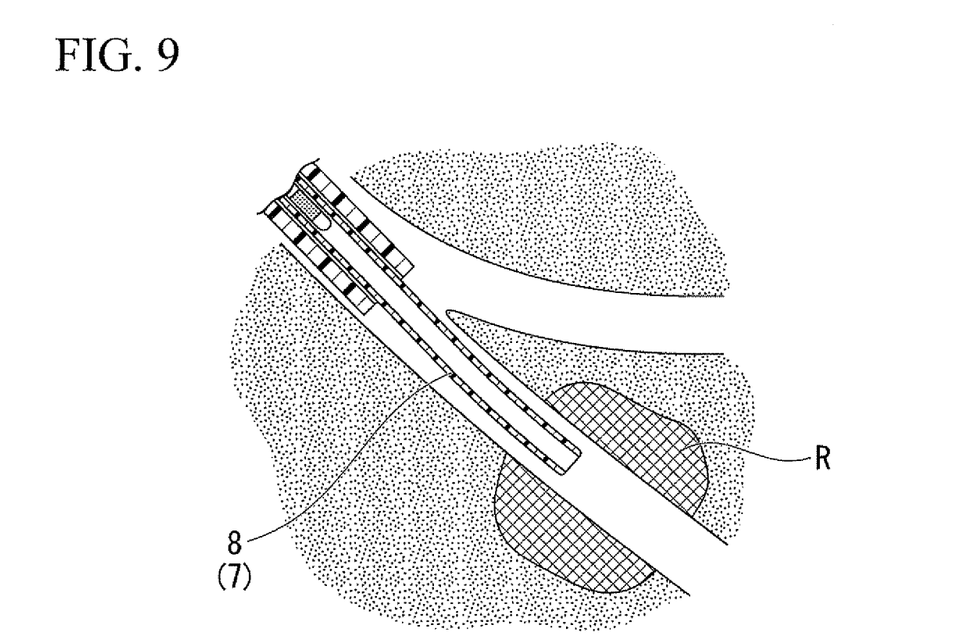
FIG. 9 is a view illustrating a state in which the guide sheath is held at the target site.

After the operator confirmed that the ultrasonic probe 102 has reached the target site R, the procedure proceeds to step S2. In step S2, the sheath body 8 is advanced to the vicinity of the target site R along the ultrasonic probe 102 as shown in FIG. 9. The position of the tip of the sheath body 8 is confirmed by the indexing member 10 (not shown).

Here, in a state in which the tip of the ultrasonic probe 102 is placed in the position where the tissue samples are to be taken, the position of the ultrasonic probe 102 projected from the rear end of the stick 9 of the guide sheath 7 is marked. Then, only the ultrasonic probe 102 is removed from the guide sheath 7 and the guide sheath 7 is held there.

Figure 10:
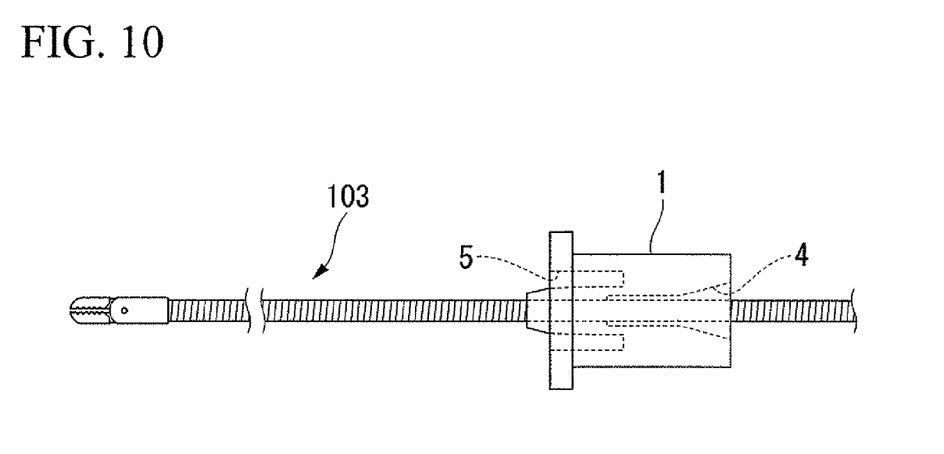
FIG. 10 is a view illustrating a state in which the marker used in the endoscopic treatment tool is attached to a biopsy cup.

In the next step S3, a known biopsy cup (endoscopic treatment tool) 103 is inserted in the insertion hole 4 from the rear end of the marker 1, and the marker 1 is fixed to the biopsy cup 103 as shown in FIG. 10. The marker 1 is then slid to a position where the distance between the rear end of the engaging groove 5 and the tip of the biopsy cup equals the distance between the tip of the ultrasonic probe 102 and the marking taken in step S2.

Instead of the biopsy cup 103, other treatment tools such as a biopsy brush may alternatively be used.

Figure 11:
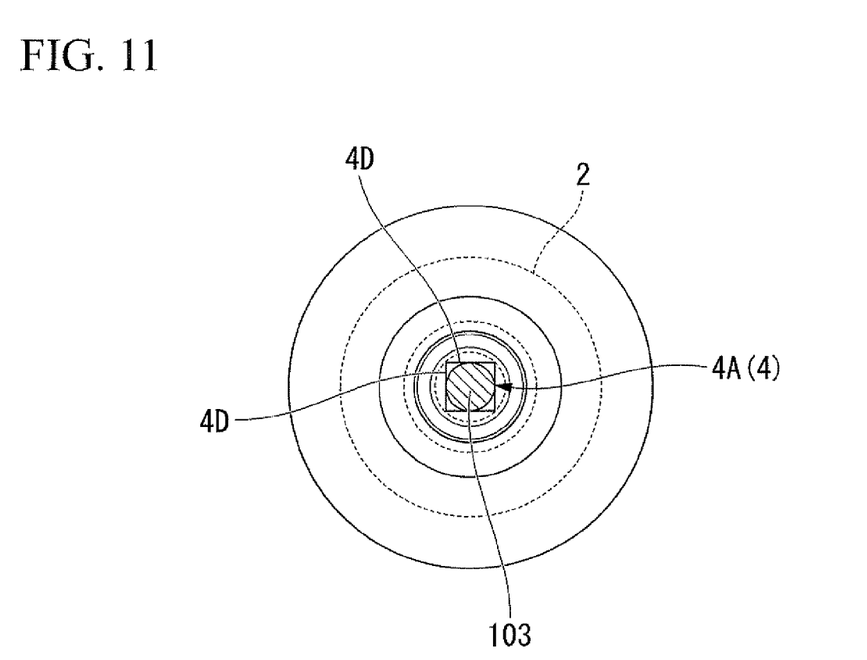
FIG. 11 is a front view of the marker used in the endoscopic treatment tool with the biopsy cup attached thereto.
Figure 12:
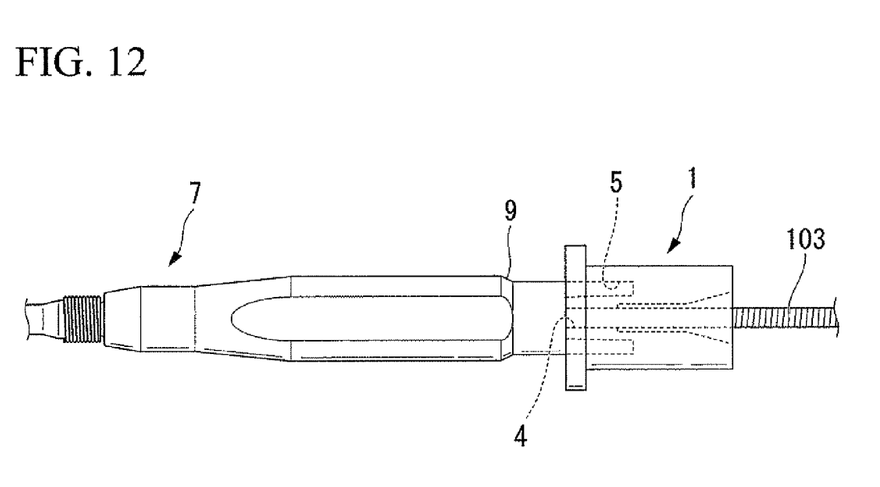
FIG. 12 is a view illustrating a state in which the marker used in the endoscopic treatment tool with the biopsy cup attached thereto is inserted in the guide sheath.

As described above, since the tip section 4A of the insertion hole 4 which functions as the fixing portion is square-sectioned, the tip section 4A is made to contact the biopsy cup 103 at four sides 4D as shown in FIG. 11. Thus, the frictional force generated between the tip section 4A and the biopsy cups 103 is small, whereby the marker 1 can be slid smoothly for positional alignment.

If the marker 1 is formed of a transparent material, the rear end of the engaging groove 5 is more clearly visible, and positioning of the marker 1 can be made more precisely.

Next, in step S4, the biopsy cup 103 to which the marker 1 is attached is inserted in the guide sheath 7 from the base end of the stick 9. Then, as shown in the dotted line in FIG. 12, the rear end of the stick 9 is made to advance into the engaging groove 5 of the marker 1, and the marker 1 is engaged in the guide sheath 7.

Figure 13:
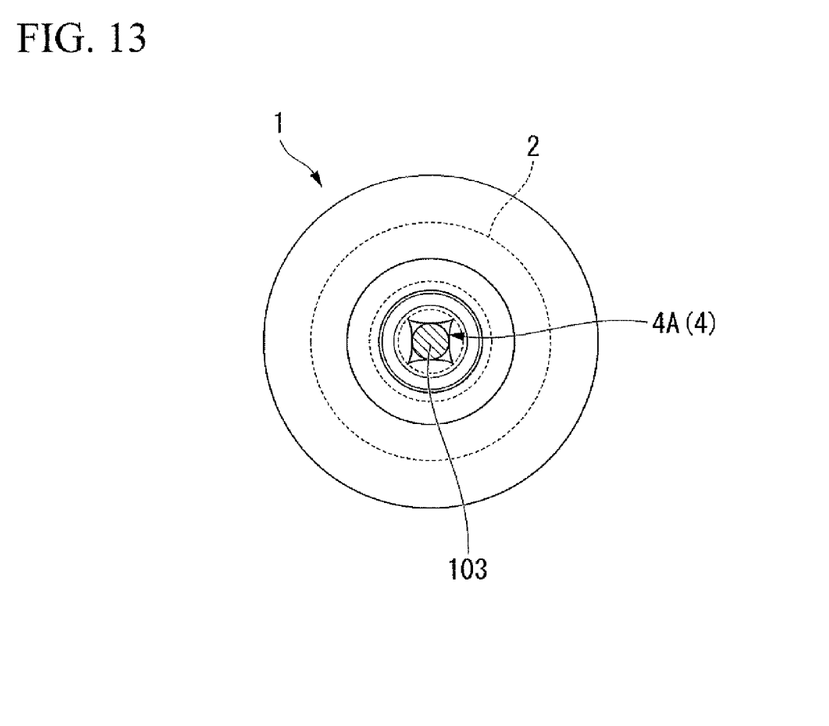
FIG. 13 is a front view illustrating a state in which the marker used in the endoscopic treatment tool with the biopsy cup attached thereto is inserted in the guide sheath.

Since the taper angle of the inner surface of the second section 12B of the through hole 12 formed in the stick 9 is larger than that of the second surface 5B of the engaging groove 5 of the marker 1, the second surface 5B of the engaging groove 5 is pressed against the insertion hole 4 as the stick 9 advances in the engaging groove 5. As a result, as shown in FIG. 13, the tip section 4A of the insertion hole 4 nips the biopsy cup 103 with far stronger force than before engagement, while keeping point contact with the biopsy cup 103. As a result, the marker 1 is securely fixed to the biopsy cup 103, and forward and backward movement of the biopsy cup 103 within the guide sheath 7 is prevented.

Figure 14:
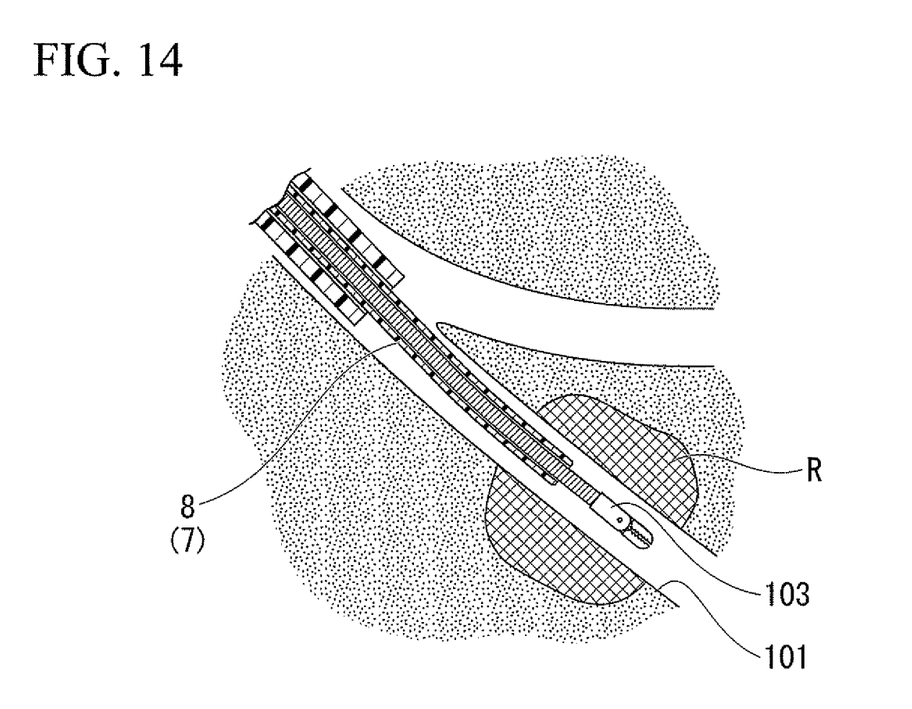
FIG. 14 is a view illustrating a state in which tissue of the target site is taken using the biopsy cup.

In the state in which the marker 1 and the stick 9 are engaged together, the biopsy cup 103 is projected only the same distance as that of the ultrasonic probe 102 in step S2 from the tip of the sheath body 8, and the tip of the biopsy cup 103 reliably reaches the target site R as shown in FIG. 14.

Here, in step S5, the biopsy cup 103 is operated to take tissue samples at the target site R. After taking the tissue samples, the biopsy cup 103 is removed and the tissue samples are collected. Taking tissue samples in step S5 may be repeated several times when needed. It is also possible to estimate the size (i.e., the length along the direction in which the bronchiole 101 extends) of the target site R by repeating taking tissue samples several times with the position of the marker 1 fine-controlled and moving the tip of the biopsy cut 103 forward and backward in order to specify the position at which no more tissue sample can be taken.

The steps shown in FIG. 5 are not necessarily performed in the described order. Instead, a projecting length of the biopsy cup 103 from the guide sheath 7 may be determined in advance, the marker 1 may be attached at a predetermined position on the biopsy cup 103 so that the biopsy cup 103 projects at the predetermined length, and then the guide sheath 7 may be disposed such that the distance between the tip of the ultrasonic probe 102 and the tip of the guide sheath 7 equals the above predetermined length while observing via X-ray radioscopy.

In step S1, instead of providing the ultrasonic probe 102, the biopsy cup 103 inserted in the guide sheath may be advanced to the target site R. Alternatively, the guide sheath 7 alone may be advanced to the target site. X-ray radioscopy, a ultrasonic image or an endoscope image may be suitably selected for guiding instruments to the target site R.

The marker 1 is attached to the biopsy cup 103 before the biopsy cup 103 is inserted in the guide sheath 7, but the marker 1 is not necessarily engaged and fixed to the stick 9 immediately after the ultrasonic probe 102 is removed. For example, the marker 1 may be engaged with the stick 9 when the tip of the biopsy cup 103 is positioned under X-ray radioscopy, thereby positioning and engagement may occur at the same time.

According to the marker 1 of the present embodiment, the positional relationship between the biopsy cup 103 and the guide sheath 7 is fixed when the engaging groove 5 of the engaging portion 3 engages the guide sheath 7. In this manner, the tip of the biopsy cup 103 can be projected precisely by the predetermined amount. Thus, the tip of the biopsy cup 103 can reliably reach the target site R, thereby performing a precise biopsy.

The marker 1 is slidably fixed to the biopsy cup 103 in the axial direction thereof due to frictional force between the inner surface of the tip section 4A of the insertion hole 4 and the outer surface of the biopsy cup 103. Thus, the projecting length of the biopsy cup 103 from the guide sheath 7 can be controlled as intended by changing the position at which the marker 1 is fixed to the biopsy cup 103.

The marker 1 and the biopsy cup 103 are in contact with each other not in the entire inner surface of the insertion hole 4, but only in the inner surface of the tip section 4A. Further, since the tip section 4A is square-sectioned as described above, the tip section 4A is made to point contact with the biopsy cup 103 only at four sides 4D. Thus, since the marker 1 is structured to have a smaller contact area with the biopsy cup 103 to be attached to, the frictional force generated between the marker 1 and the biopsy cups 103 in the axial direction is small, whereby the marker 1 can be slid smoothly for positional alignment.

The marker 1 is engaged with the stick 9 of the guide sheath 7 such that, as the stick 9 advances in the engaging groove 5, the second surface 5B of the engaging groove 5 is pressed against the insertion hole 4 due to a difference in taper angles as described above. Thus, the marker 1 is firmly fixed to the biopsy cup 103, and the positional relationship with the guide sheath 7 in operation including taking tissue samples is reliably maintained. In this manner, a marker which slides smoothly for positional alignment and is firmly fixed for engagement can be obtained.

In addition, since the flange 6 is provided in the engaging portion 3, even if the external surface of the body 2 is drawn toward the rear end side due to deformation at the time of engagement with the stick 9, the flange 6 moves toward the radial direction inner side, the movement of the entire external surface of the body 2 can be prevented. Therefore, a marker with holding performance which is not easily decline during engagement can be obtained.

While the embodiments of the invention have been described, the technical range of the invention is not limited to those described. Various modifications may be made without departing from the scope of the invention.

In the described embodiment, although the marker 1 includes the engaging portion 3 and is engaged with the base end of the guide sheath 7, an abutting portion may be provided instead of the engaging portion 3 for abutting the base end of the guide sheath 7.

In particular, if the engaging groove 5 is not provided in the marker 1, a front end surface of the body 2 abuts the base end of the guide sheath 7 and functions as the abutting portion. In this manner, when the endoscopic treatment tool with the marker attached thereon is inserted in the guide sheath and the abutting portion is made to abut the base end of the guide sheath, a predetermined length of the tip of the endoscopic treatment tool can always be projected from the tip of the guide sheath.

In the described embodiment, although the marker 1 is fixed slidably in the axial direction of the endoscopic treatment tool by the inner surface of the insertion hole 4, the invention is not limited thereto. For example, the marker 1 may be removably fixed at an intended position by nipping the endoscopic treatment tool like a clip.

In addition, neither the engaging portion nor the abutting portion is indispensable. So long as the marker is fixed to a predetermined position of the endoscopic treatment tool, when the guide sheath is inserted to the position of the marker, a predetermined length of the tip of the endoscopic treatment tool can always be projected from the tip of the guide sheath.

In addition, in the described embodiment, although the marker is attached to the endoscopic treatment tool such as the biopsy cup for taking tissue samples, the invention is not limited thereto. The marker may be attached to any treatment tools that are difficult to locate in a body.

For example, the marker of the invention may be attached to an ultrasonic probe for reliable ultrasonic image diagnosis in a position repeatedly.

What is claimed is:

1. A marker used in an endoscopic treatment tool to be inserted in a guide sheath, the marker comprising:
   a body;
   a fixing portion which is provided at the body; and
   an engaging portion which is provided at a radial direction outside of the body rather than the fixing portion of the body, wherein
   the fixing portion includes an insertion hole in which the endoscopic treatment tool is inserted,
   the engaging portion includes an engaging groove for fixing the body and the guide sheath by press-fitting a base end of the guide sheath into the engaging groove, the engaging groove formed in an annular shape and having an even surface,
   the insertion hole has a square cross-section having sides,
   in a state that the endoscopic treatment tool is inserted into the insertion hole, the endoscopic treatment tool is in contact with a part of the sides of the insertion hole and there is a clearance between a corner of the insertion hole and the endoscopic treatment tool,
   the body is fixed at a position on the endoscopic treatment tool due to a frictional force generated between the inner wall of the insertion hole and the endoscopic treatment tool such that the marker is capable of sliding relative to the endoscopic treatment tool in an axis direction of the endoscopic treatment tool,
   a projecting length of the endoscopic treatment tool from the guide sheath is capable of being changed by adjusting a fixing position of the body on the endoscopic treatment tool when the body and the guide sheath are not fixed at the engaging portion, and
   by moving the endoscopic treatment tool to which the body is fixed relative to the guide sheath, a wall surface of the engaging groove at a side of the insertion hole is pressed to a direction of the insertion hole and a fixation between the body and the endoscopic treatment tool is enhanced accompanied by the proximal end of the guide sheath being pressed into the engaging groove, and thereby restricting a change of the projecting length of the endoscopic treatment tool from the guide sheath.

2. The marker according to claim 1, wherein:
   the body is formed of an elastic material.

3. The marker according to claim 1, further comprising an abutting portion which abuts a base end of the guide sheath, wherein
   the abutting portion is made to abut the base end of the guide sheath to allow the tip of the endoscopic treatment tool to project from the tip of the guide sheath by a predetermined amount.

4. A guide sheath system for an endoscopic treatment tool comprising:
   the marker used in an endoscopic treatment tool according to claim 1; and
   a guide sheath which includes at a base end thereof a tubular engaging member which is engaged with the engaging portion.

5. The guide sheath system according to claim 4, wherein the engaging groove is provided at a radial direction outside of the insertion hole.

6. The guide sheath system according to claim 5, wherein
   a wall surface of the engaging groove at the side of the insertion hole is formed in a tapered shape such that the engaging groove has a radial direction width which becomes gradually smaller along an axial direction of the insertion hole from an end at which an engaging member enters;
   an inner surface of the engaging member is formed in a tapered shape such that a wall thickness of the engaging member becomes thicker in an axial direction of the engaging member from an end at which the engaging member enters the engaging groove; and
   a taper angle of the inner surface of the engaging member is larger than that of the taper shaped wall surface at the side of the insertion hole of the engaging groove.

* * * * *